US012674786B1

(12) United States Patent
Hadayat et al.

(10) Patent No.: US 12,674,786 B1
(45) Date of Patent: Jul. 7, 2026

(54) BIOMARKER-BASED MICROPLASTIC EXPOSURE QUANTIFICATION

(71) Applicant: Microplastics Index LLC, Dallas, TX (US)

(72) Inventors: Mohammad Ali Hadayat, Hayward, CA (US); Cody Barbo, Dallas, TX (US); Daniel Goldstein, Dallas, TX (US)

(73) Assignee: Microplastics Index LLC, Dallas, TX (US)

( * ) Notice: Subject to any disclaimer, the term of this patent is extended or adjusted under 35 U.S.C. 154(b) by 0 days.

(21) Appl. No.: 19/458,239

(22) Filed: Jan. 23, 2026

(51) Int. Cl.
　　*G01N 30/72* 　　(2006.01)
　　*G01N 30/02* 　　(2006.01)
　　　　　(Continued)

(52) U.S. Cl.
　　CPC ..... *G01N 30/7233* (2013.01); *G01N 30/8641* (2013.01); *G01N 30/8686* (2013.01);
　　　　　(Continued)

(58) Field of Classification Search
　　CPC ........... G01N 30/7233; G01N 30/8641; G01N 30/8686; G01N 30/88; G01N 2030/027;
　　　　　(Continued)

(56) References Cited

U.S. PATENT DOCUMENTS

| 2009/0095057 A1 | 4/2009 | Staats |
| 2023/0212637 A1 | 7/2023 | Kim et al. |

(Continued)

FOREIGN PATENT DOCUMENTS

| CN | 115667549 A | 1/2023 |

OTHER PUBLICATIONS

Penalver et al, "Static headspace-gas chromatography with mass spectrometry for the assessment of the bioaccumulation of volatile organic compounds associated with microplastics in animal tissues", Analytica Chimica Acta, 2025, pp. 1-10. (Year: 2025).*

(Continued)

*Primary Examiner* — Jennifer Wecker
(74) *Attorney, Agent, or Firm* — Landfall IP

(57) ABSTRACT

A method for quantifying microplastic exposure in a subject includes receiving a blood sample and measuring, using liquid chromatography-mass spectrometry, concentrations of a plurality of non-endogenous chemical biomarkers in the blood sample, wherein each biomarker is associated with at least one microplastic polymer type. The method may include comparing the measured concentrations against baseline contamination levels derived from control samples. Biomarker concentrations attributable to in-vivo microplastic exposure may be identified based at least in part on the comparing. An exposure assessment for the subject may be generated based at least in part on the biomarker concentrations, wherein the exposure assessment indicates exposure levels for one or more microplastic polymer types. The exposure levels may be categorized relative to a population reference dataset and may be mapped to likely sources of microplastic exposure.

18 Claims, 6 Drawing Sheets

(51) Int. Cl.

| | |
|---|---|
| *G01N 30/06* | (2006.01) |
| *G01N 30/86* | (2006.01) |
| *G01N 30/88* | (2006.01) |
| *G16H 10/40* | (2018.01) |
| *G16H 15/00* | (2018.01) |
| *G16H 50/70* | (2018.01) |

(52) U.S. Cl.
CPC ............. *G01N 30/88* (2013.01); *G16H 10/40* (2018.01); *G16H 15/00* (2018.01); *G16H 50/70* (2018.01); *G01N 2030/027* (2013.01); *G01N 2030/067* (2013.01); *G01N 2030/884* (2013.01)

(58) Field of Classification Search
CPC ....... G01N 2030/067; G01N 2030/884; G16H 10/40; G16H 15/00; G16H 50/70
See application file for complete search history.

(56) References Cited

U.S. PATENT DOCUMENTS

| | | | |
|---|---|---|---|
| 2023/0383346 A1 | 11/2023 | Kim et al. | |
| 2025/0281531 A1* | 9/2025 | Savage | ............... A61K 31/194 |

OTHER PUBLICATIONS

Nardella et al, "Advancing pyrolysis-gas chromatography-mass spectrometry for the accurate quantification of micro- and nanoplastics in human blood", Microplastics and Nanoplastics, 2025, pp. 1-10. (Year: 2025).*

* cited by examiner

105    User Self-Collection

110    Remote Collection Kit

115    Logistics Path

120    Centralized Laboratory

125    LC-MS Platform

130    Analysis Server

135    Exposure Profile Report

100

305

310

315

300

400

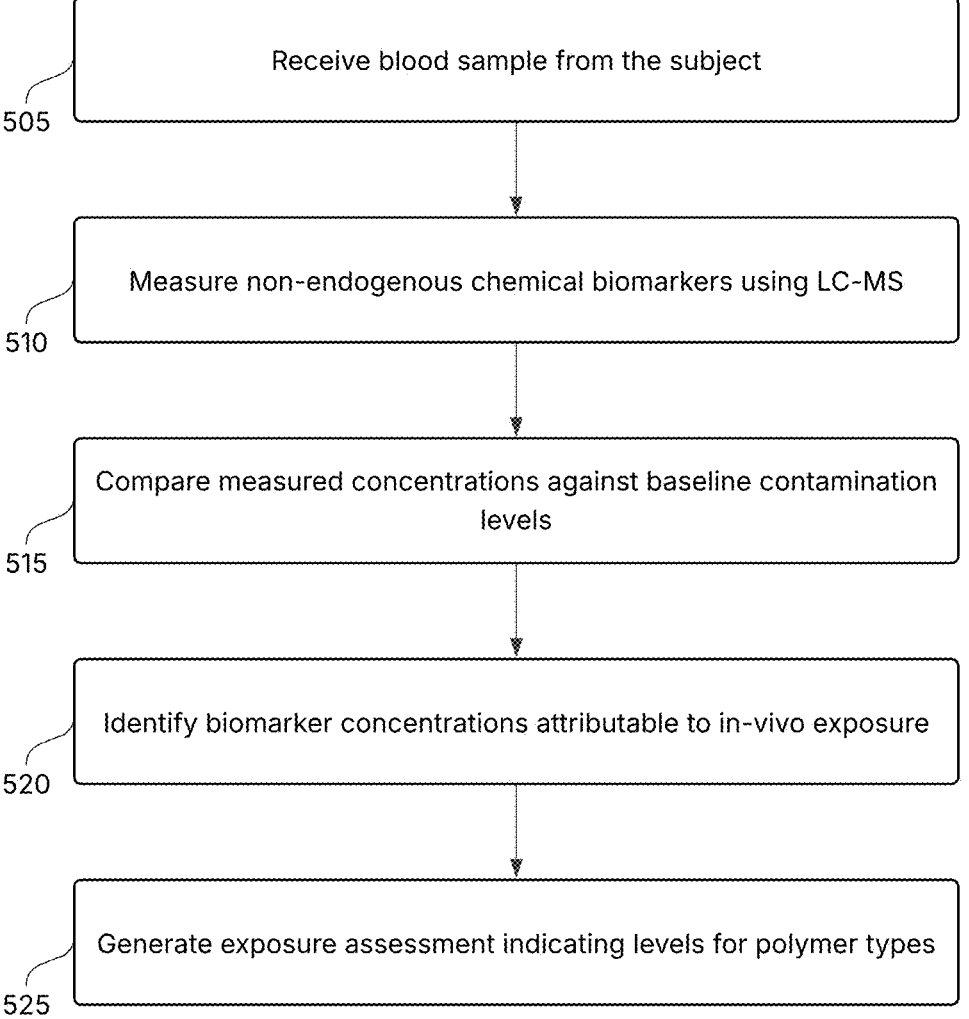
505  Receive blood sample from the subject
510  Measure non-endogenous chemical biomarkers using LC-MS
515  Compare measured concentrations against baseline contamination levels
520  Identify biomarker concentrations attributable to in-vivo exposure
525  Generate exposure assessment indicating levels for polymer types
FIG. 5                                        500

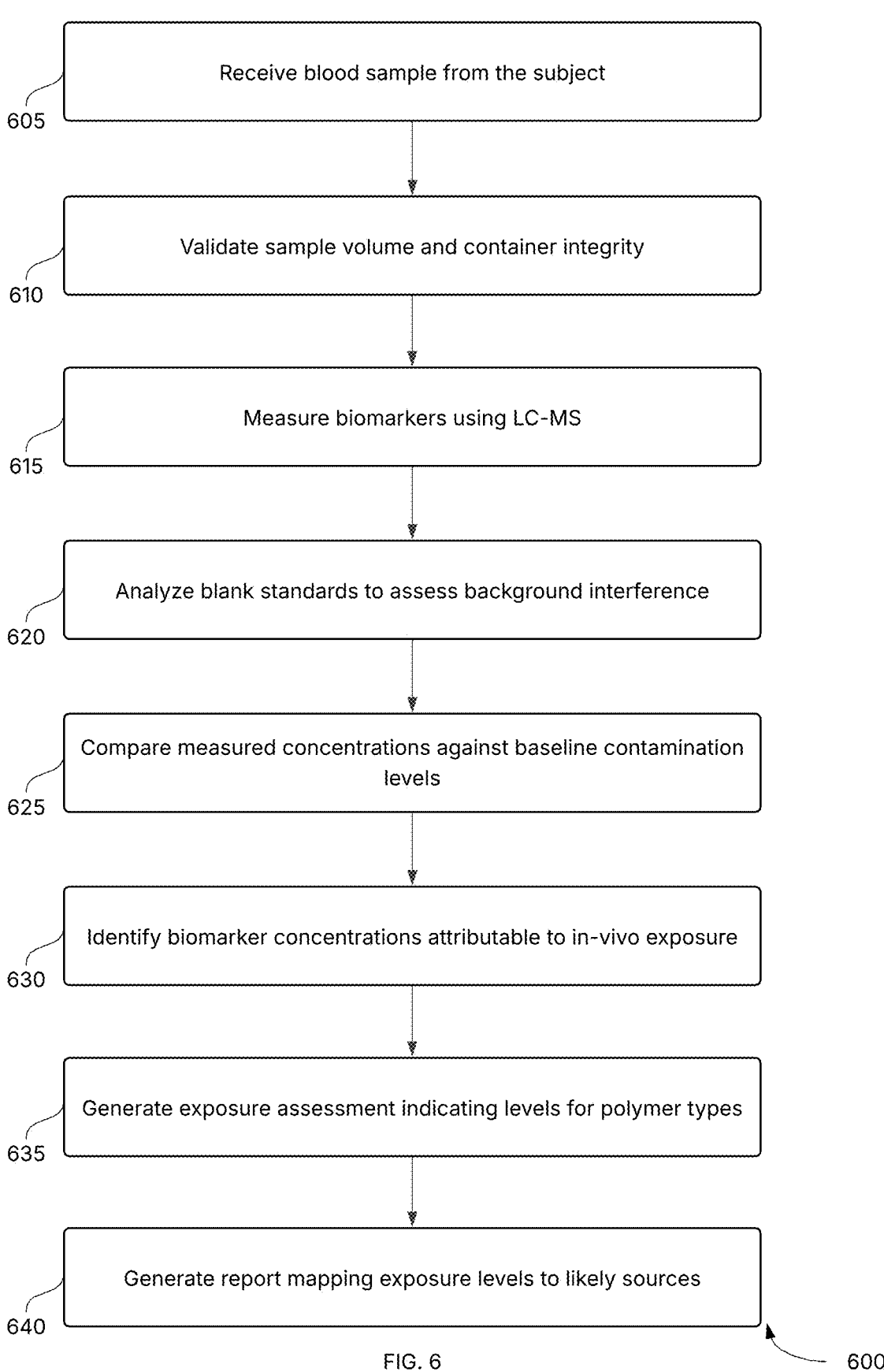

605    Receive blood sample from the subject

610    Validate sample volume and container integrity

615    Measure biomarkers using LC-MS

620    Analyze blank standards to assess background interference

625    Compare measured concentrations against baseline contamination levels

630    Identify biomarker concentrations attributable to in-vivo exposure

635    Generate exposure assessment indicating levels for polymer types

640    Generate report mapping exposure levels to likely sources

FIG. 6      600

BIOMARKER-BASED MICROPLASTIC EXPOSURE QUANTIFICATION

BACKGROUND

Microplastics and nanoplastics have become pervasive in the environment and are increasingly detected in human biological samples. Current approaches for assessing microplastic exposure in humans rely primarily on microscopy-based particle detection that directly identify polymer particles. These techniques present several limitations for widespread adoption, including low throughput, high per-sample costs, labor-intensive workflows, and dependence on subjective interpretation by trained operators. Furthermore, particle-counting outputs provide limited biological interpretability, as they do not directly quantify the concentration of microplastic-derived chemical compounds circulating in blood. The lack of scalable, objective, and quantifiable methods for assessing systemic microplastic exposure in humans has hindered the development of commercial health and wellness testing products that could inform individuals about their relative exposure levels.

SUMMARY

The described techniques relate to improved methods, systems, and non-transitory computer-readable media that support biomarker-based quantification of microplastic exposure in human subjects. In some examples, a testing system may measure concentrations of non-endogenous chemical biomarkers in blood samples using liquid chromatography-mass spectrometry (LC-MS), where each biomarker is associated with one or more microplastic polymer types. The system may compare measured concentrations against baseline contamination levels derived from control samples to distinguish biomarker signals attributable to actual in-vivo exposure from those attributable to instrumentation contamination, thereby enabling objective and scalable quantification of microplastic exposure.

Furthermore, some implementations may provide a population-based reference framework for interpreting individual exposure levels. This framework may include biomarker concentration distributions derived from profiled individuals, enabling categorization of each subject's exposure as low, medium, or high (or some other relative comparison) relative to the population. The system may generate exposure reports that map biomarker concentrations to specific polymer types, including but not limited to, polyethylene terephthalate, polystyrene, polymethyl methacrylate, polyethylene, and polypropylene, and may include behavioral recommendations for reducing exposure based on the identified polymer sources.

In addition to laboratory analysis, some implementations may provide an end-to-end workflow encompassing at-home blood collection, sample logistics, and electronic report delivery. The workflow may utilize at-home blood collection devices with pre-loaded anticoagulant, enabling consumer self-collection and shipment to centralized laboratory facilities. Through these techniques, some implementations offer a scalable solution for quantifying microplastic exposure in health and wellness applications, providing biologically relevant exposure measures rather than particle counts.

A method for quantifying microplastic exposure in a subject is disclosed. The method may include receiving a blood sample from the subject. Concentrations of a plurality of non-endogenous chemical biomarkers in the blood sample may be measured using liquid chromatography-mass spectrometry, where each biomarker of the plurality of non-endogenous chemical biomarkers is associated with at least one microplastic polymer type. The measured concentrations may be compared against baseline contamination levels derived from control samples processed through liquid chromatography-mass spectrometry. Biomarker concentrations attributable to in-vivo microplastic exposure may be identified based at least in part on the comparing. An exposure assessment for the subject may be generated based at least in part on the biomarker concentrations, where the exposure assessment indicates exposure levels for one or more microplastic polymer types.

A system for providing microplastic exposure information to a subject is disclosed. The system may include an at-home blood collection kit configured for shipment to the subject. The kit may comprise a blood collection device and a collection vial pre-loaded with an anticoagulant. The system may include a laboratory analysis system configured to receive the blood sample and to measure concentrations of a plurality of non-endogenous chemical biomarkers in the blood sample, where each biomarker of the plurality of non-endogenous chemical biomarkers is associated with at least one microplastic polymer type. The system may include a report delivery system configured to electronically transmit an exposure report to the subject. The exposure report may comprise exposure levels for one or more microplastic polymer types derived from the measured concentrations of the plurality of non-endogenous chemical biomarkers, and a categorization of each exposure level as low, medium, or high relative to a population reference dataset.

A non-transitory computer-readable medium storing instructions for quantifying microplastic exposure is disclosed. The instructions, when executed by one or more processors, may cause the one or more processors to receive biomarker concentration data comprising measured concentrations of a plurality of non-endogenous chemical biomarkers from a blood sample, where each biomarker of the plurality of non-endogenous chemical biomarkers is associated with at least one microplastic polymer type. The measured concentrations may be compared against a population reference dataset to determine exposure levels for one or more microplastic polymer types. Each exposure level may be categorized as low, medium, or high relative to the population reference dataset. An exposure report comprising the exposure levels and the categorization for each of the one or more microplastic polymer types may be generated. The exposure report may be transmitted to an electronic device associated with a subject from whom the blood sample was collected.

Some examples of the method, apparatuses, and non-transitory computer-readable medium described herein may further include operations, features, means, or instructions for the liquid chromatography-mass spectrometry comprising triple-quadrupole mass spectrometry with multiple reaction monitoring transitions optimized for each biomarker of the plurality of non-endogenous chemical biomarkers.

Some examples of the method, apparatuses, and non-transitory computer-readable medium described herein may further include operations, features, means, or instructions for the multiple reaction monitoring transitions comprising precursor ion to fragment ion transitions defined for each biomarker and configured for selective detection of each biomarker.

Some examples of the method, apparatuses, and non-transitory computer-readable medium described herein may further include operations, features, means, or instructions for the one or more microplastic polymer types comprising at least one of polyethylene terephthalate, polystyrene, or polymethyl methacrylate.

Some examples of the method, apparatuses, and non-transitory computer-readable medium described herein may further include operations, features, means, or instructions for the plurality of non-endogenous chemical biomarkers comprising at least dimethyl terephthalate, benzoic acid, and terephthalic acid (TPA) as chemical fingerprints indicative of polyethylene terephthalate exposure, at least methacrylic acid and methyl methacrylate as chemical fingerprints indicative of polymethyl methacrylate exposure, and at least styrene as a chemical fingerprint indicative of polystyrene exposure.

Some examples of the method, apparatuses, and non-transitory computer-readable medium described herein may further include operations, features, means, or instructions for categorizing the exposure levels as low, medium, or high relative to a population reference dataset.

Some examples of the method, apparatuses, and non-transitory computer-readable medium described herein may further include operations, features, means, or instructions for the population reference dataset comprising biomarker concentration distributions derived from at least 500 profiled individuals.

Some examples of the method, apparatuses, and non-transitory computer-readable medium described herein may further include operations, features, means, or instructions for generating a report that maps the exposure levels to likely sources of microplastic exposure.

Some examples of the method, apparatuses, and non-transitory computer-readable medium described herein may further include operations, features, means, or instructions for the report comprising measured concentrations of each biomarker, polymer-level exposure scores, and normalized exposure categories relative to a population.

Some examples of the method, apparatuses, and non-transitory computer-readable medium described herein may further include operations, features, means, or instructions for receiving the blood sample comprising receiving a blood sample collected using an at-home blood collection device.

Some examples of the method, apparatuses, and non-transitory computer-readable medium described herein may further include operations, features, means, or instructions for the at-home blood collection device comprising a collection vial pre-loaded with lithium heparin anticoagulant.

Some examples of the method, apparatuses, and non-transitory computer-readable medium described herein may further include operations, features, means, or instructions for validating the blood sample by verifying sufficient blood volume and container integrity prior to measuring the concentrations.

Some examples of the method, apparatuses, and non-transitory computer-readable medium described herein may further include operations, features, means, or instructions for the exposure assessment indicating exposure levels for each of polyethylene, polypropylene, polystyrene, polyethylene terephthalate, and polymethyl methacrylate based on a single blood sample.

Some examples of the method, apparatuses, and non-transitory computer-readable medium described herein may further include operations, features, means, or instructions for measuring the concentrations comprising applying calibration curves for each biomarker of the plurality of non-endogenous chemical biomarkers, where each calibration curve defines a range of linearity with low, mid, and high calibration points.

Some examples of the method, apparatuses, and non-transitory computer-readable medium described herein may further include operations, features, means, or instructions for performing quality control by analyzing blank standards to assess background interference and replicates to assess precision. The blank standards may be control samples processed identically to the blood sample and nominally free of the plurality of non-endogenous chemical biomarkers. Analyzing the blank standards may characterize baseline signals attributable to the liquid chromatography-mass spectrometry instrumentation. The baseline signals may be subtracted or statistically accounted for when identifying the biomarker concentrations attributable to in-vivo microplastic exposure.

Some examples of the method, apparatuses, and non-transitory computer-readable medium described herein may further include operations, features, means, or instructions for the measured concentrations being expressed in micrograms per milliliter.

Some examples of the method, apparatuses, and non-transitory computer-readable medium described herein may further include operations, features, means, or instructions for the report further comprising behavioral recommendations for reducing exposure to one or more of the microplastic polymer types based on the exposure levels.

Some examples of the method, apparatuses, and non-transitory computer-readable medium described herein may further include operations, features, means, or instructions for the laboratory analysis system comprising a triple-quadrupole liquid chromatography-mass spectrometry instrument configured to perform multiple reaction monitoring, where the multiple reaction monitoring comprises precursor ion to fragment ion transitions defined for each biomarker and configured for selective detection of each biomarker.

BRIEF DESCRIPTION OF FIGURES

Non-limiting and non-exhaustive examples are described with reference to the following figures.

FIG. 5 illustrates a flowchart for a method for quantifying microplastic exposure in accordance with aspects of the disclosure; and FIG. 6 illustrates a flowchart for a method for quantifying microplastic exposure from a blood sample in accordance with aspects of the disclosure.

DETAILED DESCRIPTION

The following description sets forth aspects of the present disclosure. It should be recognized, however, that such description is not intended as a limitation on the scope of the present disclosure. Rather, the description also encompasses combinations and modifications to those aspects described herein.

Aspects of the disclosure are initially described in the context of an end-to-end workflow for biomarker-based microplastic exposure quantification. Aspects are then described with reference to a biomarker quantification system and an exposure profile interface. Aspects are further illustrated by apparatus diagrams, system diagrams, and flowcharts that relate to microplastic exposure quantification and report generation.

Figure 1:
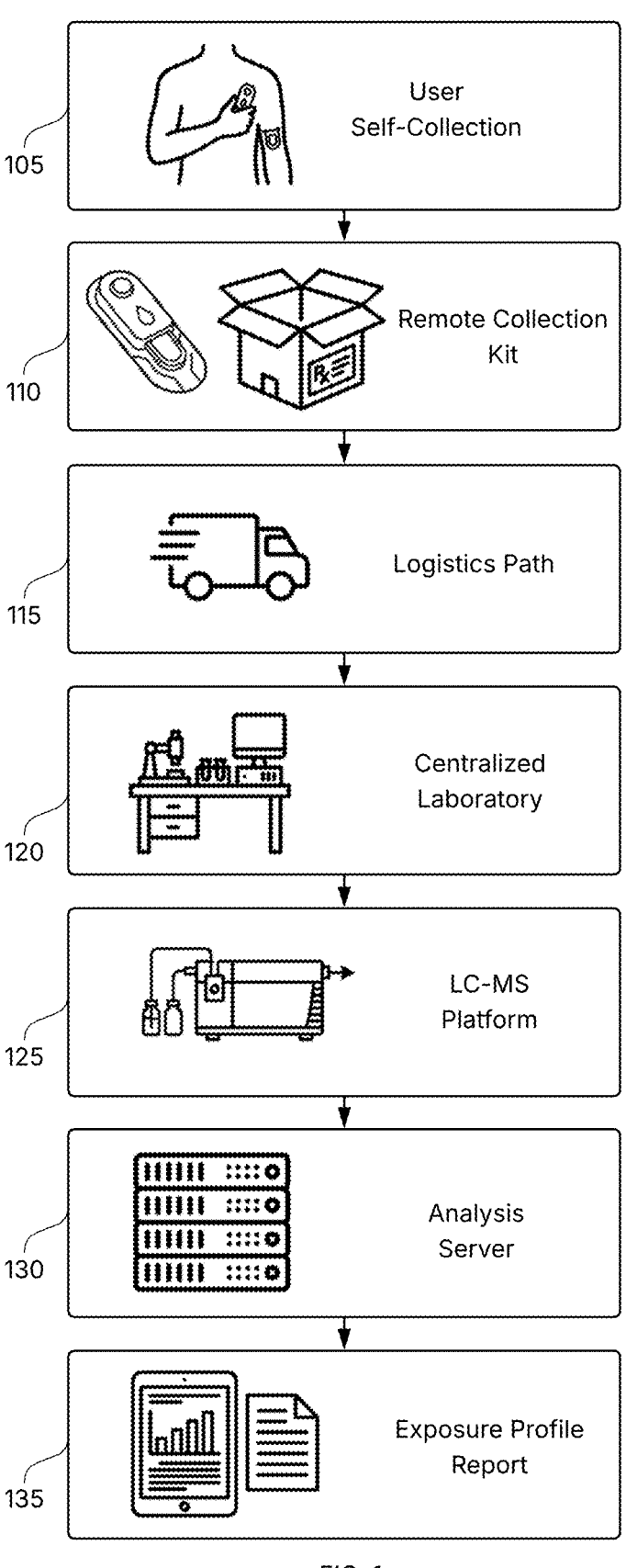
FIG. 1 illustrates a flowchart for a method for biomarker-based microplastic exposure quantification in accordance with aspects of the disclosure.

Referring to FIG. 1, a method 100 depicts an end-to-end workflow for biomarker-based microplastic exposure quantification. The method 100 may enable scalable and objective quantification of microplastic exposure for health and wellness applications by measuring concentrations of a plurality of non-endogenous chemical biomarkers in a blood sample, wherein each biomarker of the plurality of non-endogenous chemical biomarkers is associated with at least one microplastic polymer type. In some cases, the method 100 may be implemented as part of a system for providing microplastic exposure information to a subject.

The method 100 begins with a user self-collection 105, where a subject collects a blood sample using an at-home blood collection device. In some examples, receiving the blood sample may comprise receiving a blood sample collected using the at-home blood collection device. The user self-collection 105 may enable consumer-scale microplastic exposure testing without requiring phlebotomy visits. In some cases, the at-home blood collection device may be configured for upper-arm placement and may draw approximately 200-500 μL of capillary or venous blood into a collection vial. An example of such an at-home collection device is the Tasso+Kit (K1041-01-LHT-G01-RUO Lithium Heparin).

With continued reference to FIG. 1, a remote collection kit 110 contains the blood collection device and associated materials for sample preservation and return shipment. The remote collection kit 110 may comprise a blood collection device and a collection vial pre-loaded with an anticoagulant such as lithium heparin. In some examples, the at-home blood collection device comprises a collection vial pre-loaded with lithium heparin anticoagulant. The remote collection kit 110 may include a collection device configured for upper-arm placement that draws approximately 200-500 μL of capillary or venous blood into the collection vial. In some cases, the remote collection kit 110 may include custom-branded microplastics testing kit materials delivered through partnership with a sample collection device company for maintaining brand consistency in consumer-facing materials. The remote collection kit 110 may be configured for shipment to the subject as part of an at-home blood collection kit.

Following collection, the method 100 proceeds to a logistics path 115, where the collected sample is transported via mail or courier service. The logistics path 115 may include temperature-appropriate packaging for overnight shipment to preserve sample and biomarker integrity during transit.

As further shown in FIG. 1, the sample arrives at a centralized laboratory 120, where initial sample validation and preparation occur. The centralized laboratory 120 may perform sample inventory by scanning barcodes and associating metadata including patient ID, kit ID, and collection time into a laboratory information management system (LIMS). In some cases, the centralized laboratory 120 may verify sufficient blood volume and container integrity prior to performing testing or measurements (e.g., measuring concentrations of non-endogenous chemical biomarkers). The centralized laboratory 120 may be configured as a laboratory analysis system configured to receive the blood sample and to measure concentrations of non-endogenous chemical biomarkers in the blood sample.

The method 100 continues to a liquid chromatography-mass spectrometry (LC-MS) platform 125, where LC-MS analysis is performed to measure concentrations of non-endogenous chemical biomarkers in the blood sample. The LC-MS platform 125 may be configured as a dedicated triple-quadrupole liquid chromatography-mass spectrometry instrument reserved for the microplastics exposure test to ensure stability, reproducibility, and minimize cross-contamination from other lab assays. An example of the LC-MS platform 125 may be the QqQ LC-MS platform. In some examples, the LC-MS platform 125 may use optimized chromatographic gradients developed through feasibility and proof-of-concept studies involving a sufficient quantity (e.g., 50) test injections to achieve resolution of target or relevant biomarkers across their respective elution windows. The laboratory analysis system may comprise a triple-quadrupole liquid chromatography-mass spectrometry instrument configured to perform multiple reaction monitoring, wherein the multiple reaction monitoring comprises precursor ion to fragment ion transitions defined for each biomarker and configured for selective detection of each biomarker.

With continued reference to FIG. 1, the measured data is processed by an analysis server 130, which compares biomarker concentrations against population reference ranges and baseline contamination levels to determine exposure levels for various microplastic polymer types. The analysis server 130 may be associated with the centralized laboratory 120 or may be associated with a separate entity. The analysis server 130 may compare the measured concentrations against baseline contamination levels derived from control samples processed through liquid chromatography-mass spectrometry (e.g., the same machine and process used to process the patient samples). In some cases, the analysis server 130 may identify, based at least in part on the comparing, biomarker concentrations attributable to in-vivo microplastic exposure. The analysis server 130 may generate an exposure assessment for the subject based at least in part on the biomarker concentrations, wherein the exposure assessment indicates exposure levels for one or more microplastic polymer types.

The method 100 concludes with generation of an exposure profile report 135, which presents the subject with exposure levels for one or more microplastic polymer types along with categorizations relative to a population dataset. The exposure profile report 135 may comprise exposure levels for one or more microplastic polymer types derived from the measured concentrations of the plurality of non-endogenous chemical biomarkers, and a categorization of each exposure level as low, medium, or high relative to a population reference dataset. In some examples, a report delivery system may be configured to electronically transmit the exposure profile report 135 to the subject. The exposure profile report 135 may provide biologically relevant exposure measures rather than particle counts, enabling subjects to understand their relative exposure compared to a population.

Figure 2:
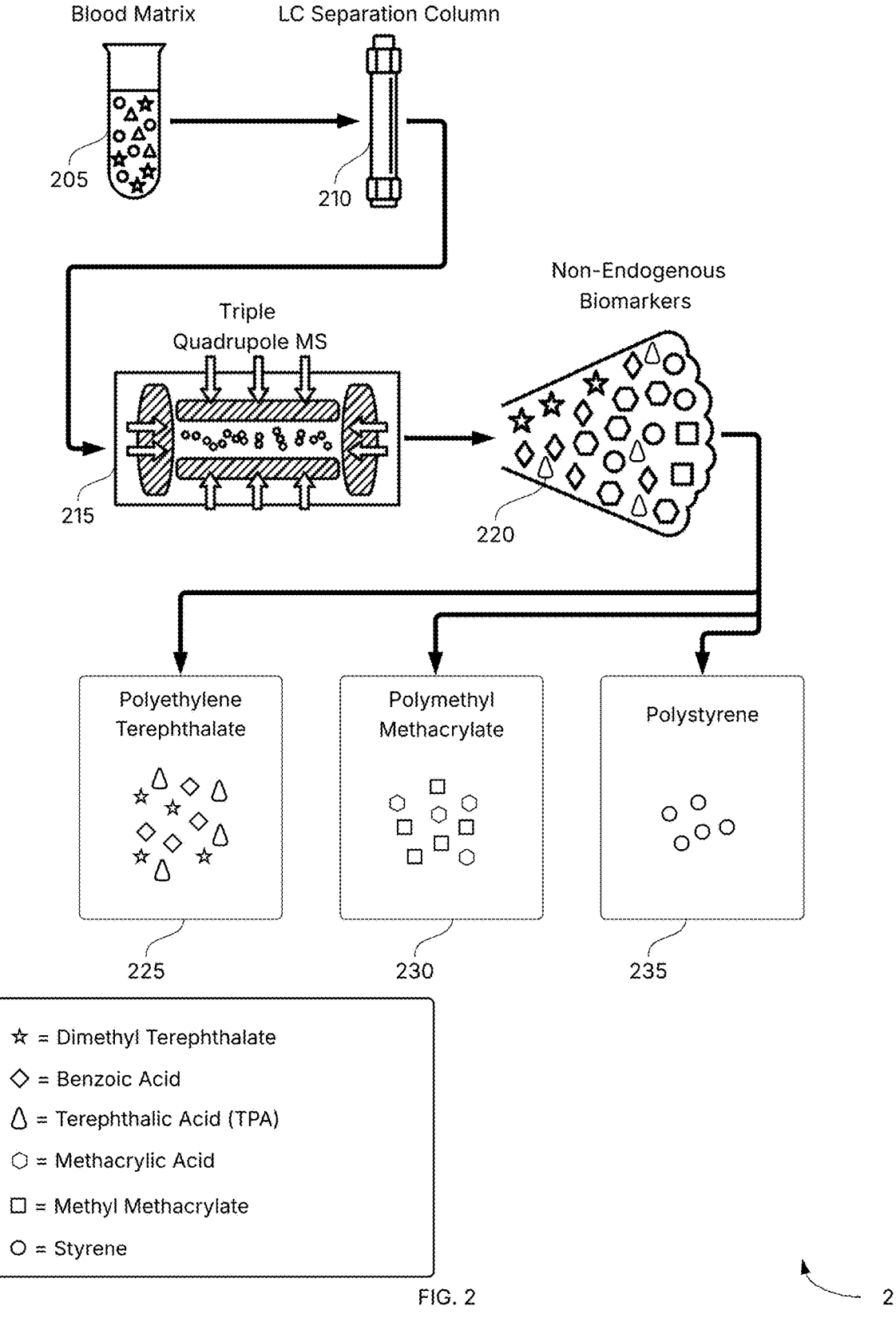
FIG. 2 illustrates a biomarker quantification system for detecting microplastic exposure through analysis of blood samples in accordance with aspects of the disclosure.

Referring to FIG. 2, a biomarker quantification system 200 for detecting microplastic exposure through analysis of blood samples is illustrated. The biomarker quantification system 200 may be configured to measure concentrations of a plurality of non-endogenous chemical biomarkers in a blood sample, wherein each biomarker of the plurality of non-endogenous chemical biomarkers is associated with at least one microplastic polymer type. In some cases, the biomarker quantification system 200 may be implemented as part of a laboratory analysis system configured to receive the blood sample from the centralized laboratory 120 described with reference to FIG. 1.

The biomarker quantification system 200 comprises a blood matrix 205 containing a mixture of compounds including multiple chemical species within the blood sample. The blood matrix 205 may undergo preparation prior to analysis, wherein the preparation includes standard blood processing steps such as plasma separation, protein precipitation, and solvent exchange to prepare the matrix for LC-MS measurement of targeted low-abundance biomarkers. Regarding plasma separation, the process may include separating the whole blood sample (between 200-500 μL from the collection device) to yield at least 60 μL of plasma. In some examples, the blood matrix 205 preparation may include digestion and other pre-analytical processing steps to extract and prepare the biomarkers for chromatographic separation. The blood matrix 205 may be processed using 96-well plate format, although other sample preparation formats such as individual vials, microcentrifuge tubes, or automated sample handling systems may be used. In some cases, the blood matrix 205 preparation may include filtration, centrifugation, solid-phase extraction, liquid-liquid extraction, or combinations thereof to isolate target compounds from the complex biological matrix.

With continued reference to FIG. 2, the blood matrix 205 is directed to an LC separation column 210, which performs liquid chromatography separation to isolate target compounds from the complex blood matrix. The LC separation column 210 may employ optimized chromatographic gradients to achieve separation of target biomarkers across their respective elution windows. In some examples, the LC separation column 210 may use solvent composition changes over time tailored so that each biomarker elutes at a distinct retention time, maximizing separation and minimizing co-elution that would confound quantification. The LC separation column 210 may be configured with gradients developed through feasibility and proof-of-concept studies to achieve resolution of the target non-endogenous chemical biomarkers.

Following separation in the LC separation column 210, the sample enters a triple quadrupole mass spectrometer 215. The triple quadrupole mass spectrometer 215 may be configured to perform multiple reaction monitoring (MRM) for selective detection of target biomarkers. In some cases, the multiple reaction monitoring comprises precursor ion to fragment ion transitions defined for each biomarker and configured for selective detection of each biomarker. The triple quadrupole mass spectrometer 215 may selectively detect target biomarkers based on their specific mass-to-charge ratios and fragmentation patterns. The liquid chromatography-mass spectrometry may comprise triple-quadrupole mass spectrometry with multiple reaction monitoring transitions optimized for each biomarker of the set of non-endogenous chemical biomarkers.

As further shown in FIG. 2, the biomarker quantification system 200 may be configured with limits of detection (LOD) and limits of quantification (LOQ) tuned to extremely low detection thresholds appropriate for trace chemical fingerprints at concentrations lower than common endogenous metabolites such as caffeine. The biomarker quantification system 200 may convert raw LC-MS signal intensities into concentrations by extracting peak areas or heights corresponding to each biomarker's retention time and MRM transitions and processing against calibration curves. In some examples, measuring the concentrations may comprise applying calibration curves for each biomarker of the plurality of non-endogenous chemical biomarkers, wherein each calibration curve defines a range of linearity with low, mid, and high calibration points. The measured concentrations may be expressed in micrograms per milliliter, although other units are possible based on the concentration levels being expressed.

The biomarker quantification system 200 measures chemical fingerprints rather than counting physical particles, thereby enabling detection across size ranges including nanoplastics and other size ranges of plastic-derived materials without requiring changes to imaging resolution or particle isolation steps. In some cases, the biomarker quantification system 200 may extend to nanoplastics and more general plastic-derived exposures because the system operates at the level of chemical signatures in blood rather than direct particle detection.

With continued reference to FIG. 2, the non-endogenous biomarkers 220 represents the collection of detected chemical fingerprints associated with microplastic exposure, as detected via the triple quadrupole mass spectrometer 215. The non-endogenous biomarkers 220 may comprise approximately 28 biomarkers, although the biomarker panel may include fewer or more biomarkers depending on the target polymer types and analytical requirements. The non-endogenous biomarkers 220 may be identified by analyzing metabolic pathways of how microplastics circulate in human blood and selecting compounds that are not naturally occurring within the human blood matrix.

The non-endogenous biomarkers 220 may be distributed across polymer types, with polyethylene having approximately 12 biomarkers, polypropylene having approximately 10 biomarkers, and polystyrene having a single biomarker. In some examples, the distribution of biomarkers reflects the breakdown chemistry of each polymer, wherein polyethylene and polypropylene generate more numerous breakdown products due to their structural complexity and multiple forms, while polyethylene terephthalate and polymethyl methacrylate produce more specific signature compounds.

As further shown in FIG. 2, the biomarker quantification system 200 categorizes the non-endogenous biomarkers 220 into polymer-specific groupings. Polyethylene terephthalate biomarkers 225 may include dimethyl terephthalate (DMT), benzoic acid, and terephthalic acid (TPA) as chemical fingerprints indicative of polyethylene terephthalate exposure. The polyethylene terephthalate biomarkers 225 are provided as a non-exhaustive example, and additional biomarkers may be associated with polyethylene terephthalate exposure.

Polymethyl methacrylate biomarkers 230 may include methacrylic acid and methyl methacrylate as chemical fingerprints indicative of polymethyl methacrylate exposure. The polymethyl methacrylate biomarkers 230 are provided as a non-exhaustive example, and additional biomarkers may be associated with polymethyl methacrylate exposure.

Polystyrene biomarkers 235 may include styrene as a chemical fingerprint indicative of polystyrene exposure. The polystyrene biomarkers 235 are provided as a non-exhaustive example, and additional biomarkers may be associated with polystyrene exposure. In some cases, the one or more microplastic polymer types may comprise at least one of polyethylene terephthalate, polystyrene, or polymethyl methacrylate, although the biomarker quantification system 200 may be configured to detect additional polymer types including polyethylene and polypropylene.

With continued reference to FIG. 2, the biomarker quantification system 200 may compute polymer-specific exposure scores by aggregating biomarker concentrations using relative weights reflecting biomarker specificity and combinatorial patterns where presence of certain biomarker subsets carries more weight. In some examples, for each polymer, the biomarker quantification system 200 may identify associated biomarkers and compute an exposure metric as a function of normalized concentration of each biomarker above baseline, relative weights that may reflect biomarker specificity or prior evidence strength, and combinatorial patterns where presence of certain biomarker subsets may carry more weight than others. The exposure assessment may indicate exposure levels for each of polyethylene, polypropylene, polystyrene, polyethylene terephthalate, and polymethyl methacrylate based on a single blood sample.

In some cases, the biomarker quantification system 200 may generate an exposure assessment for the subject based at least in part on the biomarker concentrations, wherein the exposure assessment indicates exposure levels for one or more microplastic polymer types. The exposure assessment may be categorized as low, medium, or high relative to a population reference dataset, wherein the population reference dataset comprises biomarker concentration distributions derived from at least 500 profiled individuals. The biomarker quantification system 200 may generate a report that maps the exposure levels to likely sources of microplastic exposure, wherein the report comprises measured concentrations of each biomarker, polymer-level exposure scores, and normalized exposure categories relative to a population. In some examples, the report may further comprise behavioral recommendations for reducing exposure to one or more of the microplastic polymer types based on the exposure levels.

Figure 3:
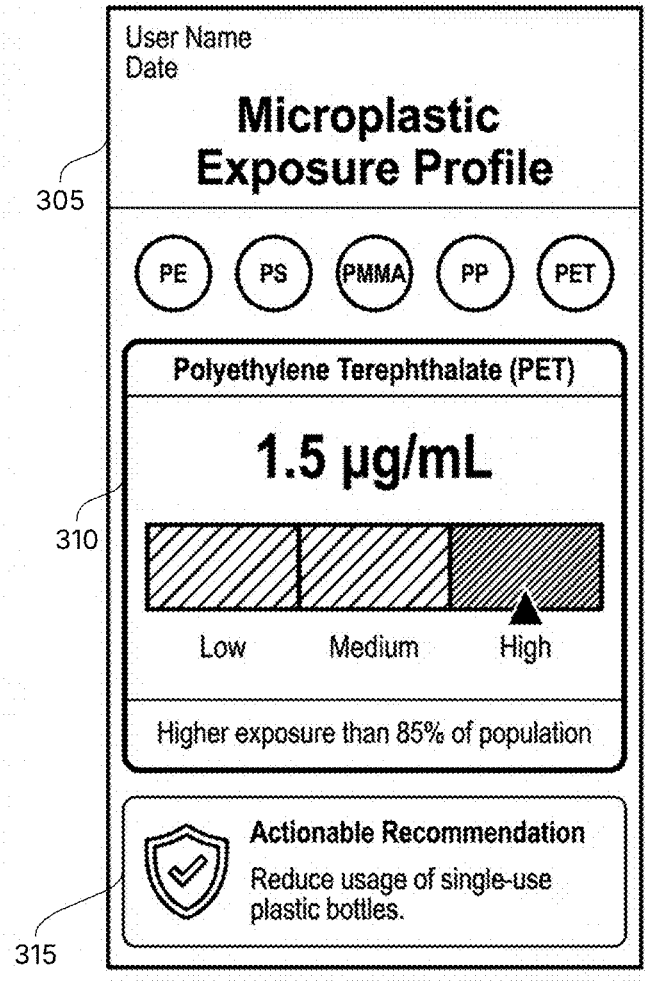
FIG. 3 illustrates an exposure profile interface displaying a microplastic exposure report in accordance with aspects of the disclosure.

Referring to FIG. 3, an exposure profile interface 300 displays a microplastic exposure report for a user. The exposure profile interface 300 may be configured to present exposure levels for one or more microplastic polymer types derived from the measured concentrations of the plurality of non-endogenous chemical biomarkers as described with reference to FIG. 2. In some cases, the exposure profile interface 300 may be implemented as part of a report delivery system configured to electronically transmit an exposure report to the subject.

The exposure profile interface 300 includes fields for user identification and date information, followed by a title indicating the report type. Below the title, polymer type indicators are shown as selectable elements labeled PE, PS, PMMA, PP, and PET, representing the different microplastic polymer types that may be assessed. In some examples, the exposure profile interface 300 may enable selection of individual polymer types to display detailed exposure information for each polymer.

With continued reference to FIG. 3, an exposure report 305 is displayed within the exposure profile interface 300, showing detailed information for polymer types with concentration measurements. The exposure report 305 may comprise measured concentrations of each biomarker, polymer-level exposure scores, and normalized exposure categories relative to a population. In some cases, the measured concentrations may be expressed in micrograms per milliliter, or in other units, as appropriate for the concentration levels being reported. Further, in some examples, the measured concentrations may be expressed as normalized values or as falling within certain ranges (e.g., low, medium, high). As shown in FIG. 3, the exposure report 305 displays a concentration measurement (e.g., 1.5 µg/mL) for polyethylene terephthalate (PET), although the exposure report 305 may display concentration measurements for any of the target polymer types and may display the measurements in other units as appropriate.

As one example of a layout, the exposure report 305 includes an exposure level indicator 310 comprising a horizontal bar divided into sections corresponding to low, medium, and high exposure categories. The exposure level indicator 310 may include a marker positioned to indicate the subject's exposure level relative to a population reference dataset. In some examples, the exposure level indicator 310 may categorize the exposure levels as low, medium, or high relative to a population reference dataset, wherein the population reference dataset comprises biomarker concentration distributions derived from a reference group (e.g., at least 500 profiled individuals).

As further shown in FIG. 3, the exposure level indicator 310 may define thresholds for low, medium, and high exposure categories based on percentile-based distributions. In some cases, the low exposure category may correspond to biomarker concentrations below the 25th percentile of the population reference dataset, the medium exposure category may correspond to biomarker concentrations between the 25th and 75th percentiles, and the high exposure category may correspond to biomarker concentrations above the 75th percentile. The exposure level indicator 310 may display text indicating the subject's relative exposure compared to the population, such as "Higher exposure than 85% of population" as shown in FIG. 3.

With continued reference to FIG. 3, an actionable recommendation section 315 is positioned within the exposure profile interface 300 to provide behavioral recommendations for reducing exposure to one or more of the microplastic polymer types based on the exposure levels. The actionable recommendation section 315 may include a visual indicator such as a shield icon and a heading followed by recommendation text. In some examples, the actionable recommendation section 315 may provide recommendations such as "Reduce usage of single-use plastic bottles" based on elevated polyethylene terephthalate exposure levels.

The actionable recommendation section 315 may include explanatory text mapping elevated signatures to likely exposure sources. In some cases, the exposure profile interface 300 may generate a report that maps the exposure levels to likely sources of microplastic exposure, wherein elevated PET-associated signatures such as dimethyl terephthalate may be indicative of frequent use of bottled water or PET-based packaging. The actionable recommendation section 315 may connect elevated signatures to specific packaging types or consumer products associated with the detected polymer types.

As further shown in FIG. 3, the exposure profile interface 300 may be configured to provide information for health and wellness use while refraining from diagnostic language or disease claims. The exposure profile interface 300 may be positioned as informational exposure data analogous to consumer genetic ancestry tests. In some examples, the exposure profile interface 300 may implement thresholding, categorization, and text generation to stay within informational use frameworks without making medical diagnosis or disease claims.

The exposure profile interface 300 may provide data in a standardized data table packaging format containing biomarker values associated with their respective polymers, quality control (QC) flags, and concentration measurements. In some cases, the standardized data table format may contain all 28 biomarker values, although the data table may contain fewer or more biomarker values depending on the biomarker panel configuration. The standardized data table format may enable downstream processing and integration with external health platforms while maintaining data quality through QC flag indicators.

Figure 4:
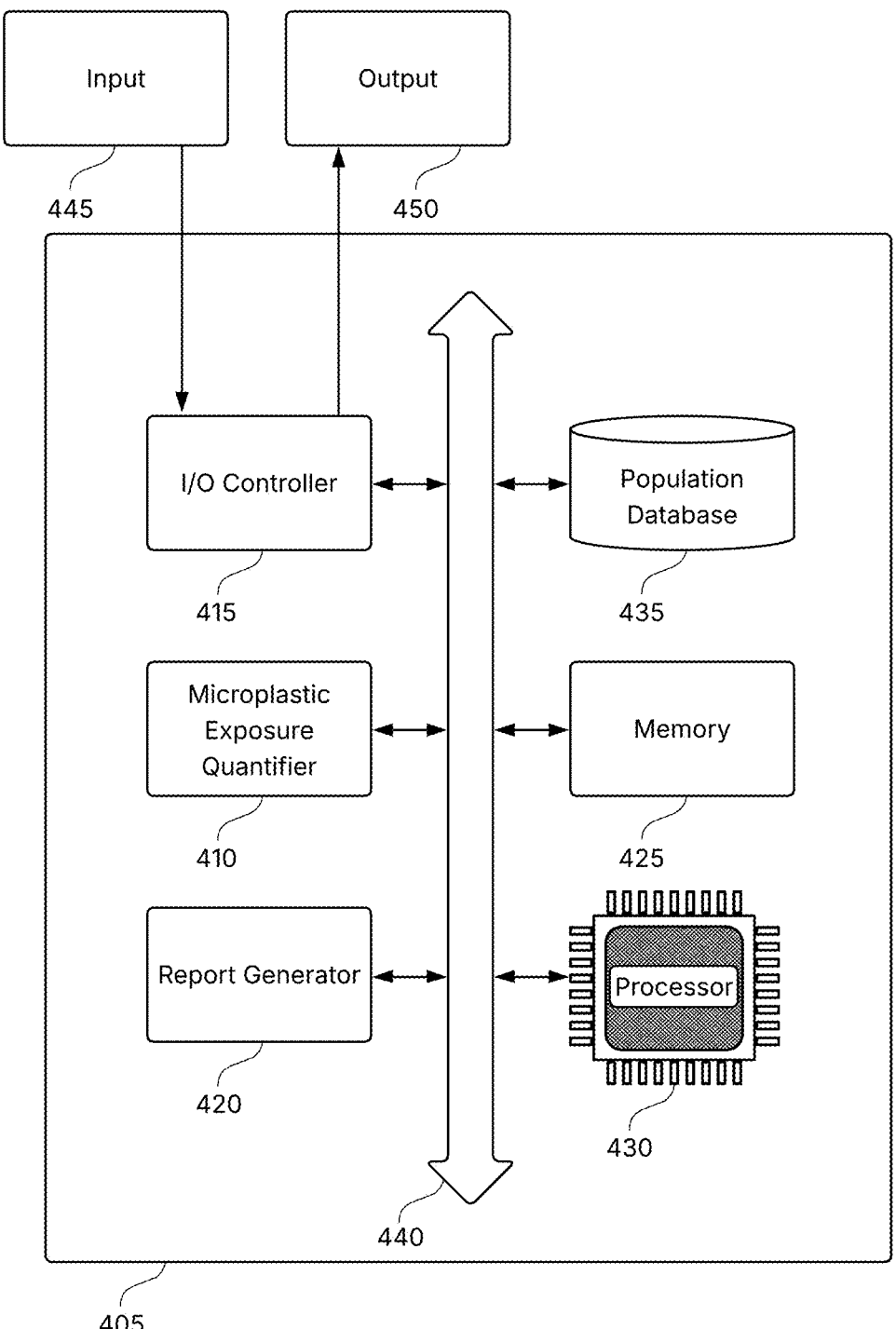
FIG. 4 is a block diagram of a microplastic exposure quantification system in accordance with aspects of the disclosure.

Referring to FIG. 4, a microplastic exposure quantification system 400 is illustrated as a block diagram depicting the architecture for processing biomarker concentration data and generating exposure assessments. The microplastic exposure quantification system 400 may be configured as a system for providing microplastic exposure information to a subject. In some cases, the microplastic exposure quantification system 400 may operate in conjunction with an at-home blood collection kit configured for shipment to the subject, the kit comprising a blood collection device and a collection vial pre-loaded with an anticoagulant, a laboratory analysis system configured to receive the blood sample and to measure concentrations of a plurality of non-endogenous chemical biomarkers in the blood sample, and a report delivery system configured to electronically transmit an exposure report to the subject.

The microplastic exposure quantification system 400 includes a microplastic exposure component 405 that houses several functional modules and processing elements. The microplastic exposure component 405 may be implemented in software, firmware, hardware, or combinations thereof. In some examples, the microplastic exposure component 405 may be implemented as instructions stored on a non-transitory computer-readable medium that, when executed by one or more processors, cause the one or more processors to perform the described functions. The microplastic exposure component 405 may receive biomarker concentration data comprising measured concentrations of a plurality of non-endogenous chemical biomarkers from a blood sample, wherein each biomarker of the plurality of non-endogenous chemical biomarkers is associated with at least one microplastic polymer type.

With continued reference to FIG. 4, the microplastic exposure component 405 comprises a microplastic exposure quantifier 410 that processes biomarker concentration data to determine exposure levels for various microplastic polymer types. The microplastic exposure quantifier 410 may compare the measured concentrations against a population reference dataset to determine exposure levels for one or more microplastic polymer types. In some cases, the microplastic exposure quantifier 410 may flag biomarker signals as indicative of in-vivo exposure when the signals exceed baseline by a defined statistical threshold such as greater than a specified number of standard deviations or above a limit of quantification (LOQ). The microplastic exposure quantifier 410 may categorize each exposure level as low, medium, or high relative to the population reference dataset.

As further shown in FIG. 4, the microplastic exposure component 405 comprises an I/O controller 415 that manages communication between the microplastic exposure component 405 and external devices. The I/O controller 415 communicates through an input 445 and an output 450. The input 445 may receive data such as biomarker concentration measurements from laboratory analysis systems including the LC-MS platform 125 described with reference to FIG. 1. The output 450 may transmit processed information such as exposure reports to external devices or systems. In some examples, the I/O controller 415 may facilitate transmission of the exposure report to an electronic device associated with a subject from whom the blood sample was collected.

With continued reference to FIG. 4, the microplastic exposure component 405 comprises a report generator 420 that creates exposure reports based on the quantified biomarker data and population comparisons. The report generator 420 may generate an exposure report comprising the exposure levels and the categorization for each of the one or more microplastic polymer types. In some cases, the report generator 420 may format the exposure assessment information for delivery through the output 450, including exposure levels for one or more microplastic polymer types and behavioral recommendations for reducing exposure as described with reference to the actionable recommendation section 315 shown in FIG. 3. The report generator 420 may generate the exposure report 305 and the exposure level indicator 310 as described with reference to the exposure profile interface 300.

As further shown in FIG. 4, the microplastic exposure component 405 comprises a memory 425 that stores instructions, calibration data, biomarker-polymer associations, and other information used during operation. The memory 425 may store calibration curves for each biomarker of the plurality of non-endogenous chemical biomarkers, wherein each calibration curve defines a range of linearity with low, mid, and high calibration points. In some examples, the memory 425 may store biomarker-polymer mapping schemas that associate each biomarker with one or more microplastic polymer types including polyethylene terephthalate, polystyrene, polymethyl methacrylate, polyethylene, and polypropylene. The memory 425 may comprise non-transitory computer-readable media storing instructions that, when executed by one or more processors, cause the one or more processors to perform the described functions.

With continued reference to FIG. 4, the microplastic exposure component 405 comprises a processor 430 that executes computational operations and coordinates the functions of the various components within the microplastic exposure component 405. The processor 430 may execute instructions stored in the memory 425 to process biomarker concentration data, compare measured concentrations against baseline contamination levels, and generate exposure assessments. In some cases, the processor 430 may implement the statistical threshold comparisons performed by the microplastic exposure quantifier 410.

As further shown in FIG. 4, the microplastic exposure component 405 comprises a population database 435 that stores reference range data derived from profiled individuals. The population database 435 may store biomarker concentration distributions derived from at least 500 profiled individuals, enabling comparison of individual biomarker concentrations against population distributions to categorize exposure levels as low, medium, or high. In some examples, the population database 435 may store empirical distributions including median, quartiles, and percentiles for each biomarker and each polymer-specific exposure score across the profiled cohort.

With continued reference to FIG. 4, the components within the microplastic exposure component 405 are interconnected via a system bus 440 that facilitates communication and data transfer between the various elements. The system bus 440 may enable the microplastic exposure quantifier 410 to access reference range data from the population database 435, calibration data from the memory 425, and input data from the I/O controller 415. The system bus 440 may enable the report generator 420 to receive exposure level determinations from the microplastic exposure quantifier 410 and transmit generated reports through the I/O controller 415.

The microplastic exposure quantification system 400 may integrate with an e-commerce platform for order management with sample ID generation and barcode tracking integrated with kit fulfillment and laboratory analysis partners. In some cases, the microplastic exposure quantification system 400 may receive sample identification data through the input 445 and associate the sample identification data with biomarker concentration measurements received from the laboratory analysis system.

The microplastic exposure quantification system 400 may be configured to support future addition of polytetrafluoroethylene (PTFE) detection using an alternative gas chromatography-based workflow while maintaining a biomarker-based interpretation framework implemented by the microplastic exposure quantifier 410. In some cases, the microplastic exposure quantification system 400 may receive PTFE-related biomarker data through the input 445 from a complementary measurement module and process the PTFE-related biomarker data using the same exposure quantification and categorization functions.

With continued reference to FIG. 4, the microplastic exposure quantification system 400 may be designed to support a future phase combining microplastic exposure signatures with sequencing-derived or other molecular markers of inflammation, oxidative stress, or cardiovascular risk from the same blood draw. The blood sample volume of approximately 500 μL may exceed the volume required for the LC-MS biomarker panel, allowing potential parallel tests such as sequencing from the same sample. In some examples, the microplastic exposure quantifier 410 may correlate microplastic polymer exposure scores with additional signatures to build diagnostic or risk-stratification models.

The microplastic exposure quantification system 400 may organize exposure data into a structured data model that can be securely surfaced via application programming interfaces (APIs) to external health AI platforms including large language model-based health assistants. In some cases, the output 450 may transmit processed results including raw biomarker concentrations, baseline-corrected values, polymer exposure scores, percentiles, and categories to external health AI ecosystems for personalized coaching, recommendations, or risk communication.

Referring to FIG. 5, a method 500 for quantifying microplastic exposure is illustrated as a flowchart depicting a sequential process for measuring and assessing microplastic exposure from a blood sample. The method 500 may be performed by the microplastic exposure quantification system 400 described with reference to FIG. 4, the biomarker quantification system 200 described with reference to FIG. 2, or by the LC-MS platform 125 and the analysis server 130 described with reference to FIG. 1. In some cases, the method 500 may enable objective quantification of microplastic exposure by distinguishing between biomarker signals attributable to actual in-vivo exposure and those attributable to baseline contamination from analytical instrumentation.

The method 500 begins at 505, where a blood sample is received from the subject. In some examples, receiving the blood sample may comprise receiving a blood sample collected using an at-home blood collection device as described with reference to the remote collection kit 110 shown in FIG. 1. The blood sample may be received at the centralized laboratory 120 where initial sample validation and preparation occur prior to analysis.

With continued reference to FIG. 5, the method 500 proceeds to 510, where non-endogenous chemical biomarkers are measured using liquid chromatography-mass spectrometry. In some cases, measuring the concentrations may comprise applying calibration curves for each biomarker of the plurality of non-endogenous chemical biomarkers, wherein each calibration curve defines a range of linearity with low, mid, and high calibration points. The calibration curves may be established using compound mixtures spanning defined concentration ranges to determine accuracy and recovery across the working range for each biomarker. The LC-MS platform 125 may convert raw signal intensities into concentrations by processing against the calibration curves to calculate the absolute concentration of each biomarker.

As further shown in FIG. 5, the method 500 continues to 515, where the measured concentrations are compared against baseline contamination levels derived from control samples processed through liquid chromatography-mass spectrometry. The LC-MS platform 125 may use control plates or control fluids processed identically to patient samples to characterize baseline plastic-related signals attributable to the lab environment and instrumentation. In some examples, the baseline signals may be computed as mean and variance across control wells, enabling statistical characterization of contamination levels for each biomarker. The control samples may be nominally free of target microplastic-derived biomarkers and may serve to characterize plastic-related background signals introduced by the laboratory environment and instrumentation.

With continued reference to FIG. 5, the method 500 proceeds to 520, where biomarker concentrations attributable to in-vivo microplastic exposure are identified based at least in part on the comparing performed at 515. In some cases, biomarker signals may be flagged as indicative of in-vivo exposure when the signals exceed baseline by a defined statistical threshold. The microplastic exposure quantifier 410 may identify biomarker concentrations that exceed the baseline contamination levels by a statistically significant amount, thereby isolating microplastic exposure signatures present in the blood from contamination inherent in the LC-MS platform 125.

As further shown in FIG. 5, the method 500 concludes at 525, where an exposure assessment is generated for the subject based at least in part on the biomarker concentrations. The exposure assessment may indicate exposure levels for one or more microplastic polymer types, including but not limited to, polyethylene, polypropylene, polystyrene, polyethylene terephthalate, and polymethyl methacrylate. In some examples, the exposure assessment may be generated based on a single blood sample and may provide exposure levels for each of the five polymer types. The report generator 420 may format the exposure assessment for delivery to the subject as described with reference to the exposure profile interface 300 shown in FIG. 3.

The LC-MS platform 125 may include routine quality control (QC) runs to verify that limits of detection (LOD), limits of quantification (LOQ), retention times, and response factors remain within acceptable ranges during high-throughput operation. In some cases, the routine QC verification runs may be performed at defined intervals during sample processing to ensure analytical performance remains consistent across batches. The QC runs may include analysis of blank standards to assess background interference and replicates to assess precision.

With continued reference to FIG. 5, the method 500 may be implemented using a systematic approach to LC-MS method optimization including gradient optimization, compound mixture preparation for calibration, and formal method transfer procedures. In some examples, the method transfer protocol may include transfer from a general LC-MS platform used during feasibility and proof-of-concept studies to a dedicated production instrument reserved for the microplastics exposure test. The method transfer procedures may ensure that the optimized gradients, multiple reaction monitoring transitions, and calibration parameters are reproducibly implemented on the dedicated triple quadrupole mass spectrometer 215 for production-scale operation.

Referring to FIG. 6, a method 600 for quantifying microplastic exposure from a blood sample is illustrated as a flowchart depicting a sequential process with additional validation and quality control steps. The method 600 may be performed by the microplastic exposure quantification system 400 described with reference to FIG. 4, the biomarker quantification system 200 described with reference to FIG. 2, or by the LC-MS platform 125 and the analysis server 130 described with reference to FIG. 1. In some cases, the method 600 may provide enhanced sample quality assurance and contamination correction compared to the method 500 described with reference to FIG. 5.

The method 600 begins at 605, where a blood sample is received from the subject. In some examples, receiving the blood sample may comprise receiving a blood sample collected using an at-home blood collection device as described with reference to the remote collection kit 110 shown in FIG. 1. The blood sample may be received at the centralized laboratory 120 where initial sample processing occurs. In some cases, the blood sample may be received via the logistics path 115 following the user self-collection 105.

With continued reference to FIG. 6, the method 600 proceeds to 610, where the sample volume and container integrity are validated. In some cases, validating the blood sample may comprise verifying sufficient blood volume and container integrity prior to measuring the concentrations of non-endogenous chemical biomarkers. The validation at 610 may include checking for leaks, damage, or other container integrity issues that could compromise sample quality. In some examples, the centralized laboratory 120 may perform barcode scanning and verification of sufficient volume as part of the validation at 610. The validation at 610 may ensure that the blood sample meets quality requirements before proceeding to analytical processing.

As further shown in FIG. 6, the method 600 continues to 615, where biomarkers are measured using liquid chromatography-mass spectrometry. In some cases, measuring the concentrations may comprise measuring, using liquid chromatography-mass spectrometry, concentrations of a plurality of non-endogenous chemical biomarkers in the blood sample, wherein each biomarker of the plurality of non-endogenous chemical biomarkers is associated with at least one microplastic polymer type. The LC-MS platform 125 may perform the measurement at 615 using the triple quadrupole mass spectrometer 215 with multiple reaction monitoring transitions as described with reference to FIG. 2. The biomarker quantification system 200 may process the blood matrix 205 through the LC separation column 210 prior to mass spectrometric detection.

With continued reference to FIG. 6, the method 600 proceeds to 620, where blank standards are analyzed to assess background interference. In some examples, performing quality control may comprise analyzing blank standards to assess background interference and replicates to assess precision. The blank standards may be control samples processed identically to the blood sample and nominally free of the plurality of non-endogenous chemical biomarkers. In some cases, the blank standards may be processed through the same LC-MS platform 125 using the same plastic-containing consumables such as 96-well plates and tubing to characterize plastic-related background signals introduced by the laboratory environment and instrumentation.

As further shown in FIG. 6, the method 600 continues to 625, where measured concentrations are compared against baseline contamination levels derived from control samples processed through liquid chromatography-mass spectrometry. In some cases, analyzing the blank standards may characterize baseline signals attributable to the liquid chromatography-mass spectrometry instrumentation. The comparison at 625 may compute baseline contamination levels including mean and variance of signal across control wells for each biomarker. The analysis server 130 may perform the comparison at 625 to distinguish between signals attributable to the LC-MS platform 125 and signals attributable to in-vivo microplastic exposure.

With continued reference to FIG. 6, the method 600 proceeds to 630, where biomarker concentrations attributable to in-vivo microplastic exposure are identified based at least in part on the comparing performed at 625. In some examples, the baseline signals may be subtracted or statistically accounted for when identifying the biomarker concentrations attributable to in-vivo microplastic exposure. The microplastic exposure quantifier 410 may flag biomarker signals as indicative of in-vivo exposure when the signals exceed baseline by a defined statistical threshold. In some cases, signals indistinguishable from baseline may be treated as undetectable above system background, while signals exceeding baseline by a statistically significant amount may be attributed to actual microplastic exposure in the subject.

As further shown in FIG. 6, the method 600 continues to 635, where an exposure assessment indicating levels for polymer types is generated. In some cases, generating an exposure assessment for the subject may be based at least in part on the biomarker concentrations identified at 630, wherein the exposure assessment indicates exposure levels for one or more microplastic polymer types. The report generator 420 may generate the exposure assessment at 635 by aggregating biomarker concentrations into polymer-specific exposure scores for one or more microplastic polymer types (e.g., polyethylene, polypropylene, polystyrene, polyethylene terephthalate, and polymethyl methacrylate). The exposure assessment may categorize each exposure level as low, medium, or high relative to the population database 435.

With continued reference to FIG. 6, the method 600 concludes at 640, where a report mapping exposure levels to likely sources is generated. In some examples, the report may comprise measured concentrations of each biomarker, polymer-level exposure scores, and normalized exposure categories relative to a population. The report generator 420 may format the report for delivery through the output 450 as described with reference to FIG. 4. In some cases, the report may include behavioral recommendations for reducing exposure to one or more of the microplastic polymer types based on the exposure levels, such as reducing use of single-use plastic bottles for elevated polyethylene terephthalate exposure as described with reference to the actionable recommendation section 315 shown in FIG. 3. The report generated at 640 may be transmitted to the subject via the exposure profile interface 300 as the exposure report 305 with the exposure level indicator 310.

It should be noted that the methods described herein describe possible implementations, and that the operations and the steps may be rearranged or otherwise modified and that other implementations are possible. Further, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

The invention claimed is:

1. A method for quantifying microplastic exposure in a subject, comprising:

receiving a blood sample from the subject;

measuring, using liquid chromatography-mass spectrometry, concentrations of a plurality of non-endogenous chemical biomarkers in the blood sample, wherein each biomarker of the plurality of non-endogenous chemical biomarkers is associated with at least one microplastic polymer type, and wherein the one or more microplastic polymer types comprise at least one of polyethylene terephthalate, polystyrene, or polymethyl methacrylate, and further wherein the plurality of non-endogenous chemical biomarkers comprises at least dimethyl terephthalate, benzoic acid, and terephthalic acid (TPA) as chemical fingerprints indicative of polyethylene terephthalate exposure, at least methacrylic acid and methyl methacrylate as chemical fingerprints indicative of polymethyl methacrylate exposure, and at least styrene as a chemical fingerprint indicative of polystyrene exposure;

comparing the measured concentrations against baseline contamination levels derived from control samples processed through liquid chromatography-mass spectrometry;

identifying, based at least in part on the comparing, biomarker concentrations attributable to in-vivo microplastic exposure; and generating an exposure assessment for the subject based at least in part on the biomarker concentrations, wherein the exposure assessment indicates exposure levels for one or more microplastic polymer types.

2. The method of claim 1, wherein the liquid chromatography-mass spectrometry comprises triple-quadrupole mass spectrometry with multiple reaction monitoring transitions optimized for each biomarker of the plurality of non-endogenous chemical biomarkers.

3. The method of claim 2, wherein the multiple reaction monitoring transitions comprise precursor ion to fragment ion transitions defined for each biomarker and configured for selective detection of each biomarker.

4. The method of claim 1, further comprising categorizing the exposure levels as low, medium, or high relative to a population reference dataset.

5. The method of claim 4, wherein the population reference dataset comprises biomarker concentration distributions derived from at least 500 profiled individuals.

6. The method of claim 1, further comprising generating a report that maps the exposure levels to likely sources of microplastic exposure.

7. The method of claim 6, wherein the report comprises measured concentrations of each biomarker, polymer-level exposure scores, and normalized exposure categories relative to a population.

8. The method of claim 1, wherein receiving the blood sample comprises receiving a blood sample collected using an at-home blood collection device.

9. The method of claim 8, wherein the at-home blood collection device comprises a collection vial pre-loaded with lithium heparin anticoagulant.

10. The method of claim 1, further comprising validating the blood sample by verifying sufficient blood volume and container integrity prior to measuring the concentrations.

11. The method of claim 1, wherein the exposure assessment indicates exposure levels for each of polyethylene, polypropylene, polystyrene, polyethylene terephthalate, and polymethyl methacrylate based on a single blood sample.

12. The method of claim 1, wherein measuring the concentrations comprises applying calibration curves for each biomarker of the plurality of non-endogenous chemical biomarkers, wherein each calibration curve defines a range of linearity with low, mid, and high calibration points.

13. The method of claim 1, further comprising performing quality control by analyzing blank standards to assess background interference and replicates to assess precision, wherein the blank standards are control samples processed identically to the blood sample and nominally free of the plurality of non-endogenous chemical biomarkers, wherein analyzing the blank standards characterizes baseline signals attributable to the liquid chromatography-mass spectrometry instrumentation, and wherein the baseline signals are subtracted or statistically accounted for when identifying the biomarker concentrations attributable to in-vivo microplastic exposure.

14. The method of claim 1, wherein the measured concentrations are expressed in micrograms per milliliter.

15. The method of claim 6, wherein the report further comprises behavioral recommendations for reducing exposure to one or more of the microplastic polymer types based on the exposure levels.

16. A system for providing microplastic exposure information to a subject, comprising:

an at-home blood collection kit configured for shipment to the subject, the kit comprising a blood collection device and a collection vial pre-loaded with an anticoagulant;

a laboratory analysis system configured to receive a blood sample and to measure concentrations of a plurality of non-endogenous chemical biomarkers in the blood sample, wherein each biomarker of the plurality of non-endogenous chemical biomarkers is associated with at least one microplastic polymer type, and wherein the one or more microplastic polymer types comprise at least one of polyethylene terephthalate, polystyrene, or polymethyl methacrylate, and further wherein the plurality of non-endogenous chemical biomarkers comprises at least dimethyl terephthalate, benzoic acid, and terephthalic acid (TPA) as chemical fingerprints configured to be indicative of polyethylene terephthalate exposure, at least methacrylic acid and methyl methacrylate as chemical fingerprints configured to be indicative of polymethyl methacrylate exposure, and at least styrene as a chemical fingerprint configured to be indicative of polystyrene exposure;

and a report delivery system configured to electronically transmit an exposure report to the subject, wherein the exposure report comprises: exposure levels for one or more microplastic polymer types derived from the measured concentrations of the plurality of non-endogenous chemical biomarkers, and a categorization of each exposure level as low, medium, or high relative to a population reference dataset.

17. The system of claim 16, wherein the laboratory analysis system comprises a triple-quadrupole liquid chromatography-mass spectrometry instrument configured to perform multiple reaction monitoring, wherein the multiple reaction monitoring comprises precursor ion to fragment ion transitions defined for each biomarker and configured for selective detection of each biomarker.

18. A non-transitory computer-readable medium storing instructions that, when executed by one or more processors, is configured to cause the one or more processors to:

receive biomarker concentration data comprising measured concentrations of a plurality of non-endogenous chemical biomarkers from a blood sample, wherein each biomarker of the plurality of non-endogenous chemical biomarkers is associated with at least one microplastic polymer type, and wherein the one or more microplastic polymer types comprise at least one of polyethylene terephthalate, polystyrene, or polymethyl methacrylate, and further wherein the plurality of non-endogenous chemical biomarkers comprises at least dimethyl terephthalate, benzoic acid, and terephthalic acid (TPA) as chemical fingerprints indicative of polyethylene terephthalate exposure, at least methacrylic acid and methyl methacrylate as chemical fingerprints indicative of polymethyl methacrylate exposure, and at least styrene as a chemical fingerprint indicative of polystyrene exposure;

compare the measured concentrations against a population reference dataset to determine exposure levels for one or more microplastic polymer types;

categorize each exposure level as low, medium, or high relative to the population reference dataset;

generate, based at least in part on the measured concentration comparison, an exposure report comprising the exposure levels and a categorization for each of the one or more microplastic polymer types; and transmit the exposure report to an electronic device associated with a subject from whom the blood sample was collected.

\* \* \* \* \*